United States Patent [19]

Wisdom

[11] Patent Number: 4,767,541
[45] Date of Patent: Aug. 30, 1988

[54] METHOD OF REMOVING PLATELETS AND WHITE CELLS FROM A RED CELL CONCENTRATE

[75] Inventor: Leonard A. Wisdom, Balgowlah, Australia

[73] Assignee: Miles Laboratories, Inc., Elkhart, Ind.

[21] Appl. No.: 864,229

[22] Filed: May 19, 1986

Related U.S. Application Data

[62] Division of Ser. No. 385,167, Jun. 4, 1982, Pat. No. 4,596,657.

[51] Int. Cl.⁴ .................. B01D 21/26; B01D 36/00
[52] U.S. Cl. .................................. 210/749; 210/787; 210/806; 422/41; 422/44
[58] Field of Search ............... 210/765, 787, 805, 749, 210/806; 422/41, 44

[56] References Cited

U.S. PATENT DOCUMENTS 3,064,647 11/1962 Earl ........................................ 422/44
3,246,767 4/1966 Pall et al. ............................. 210/505
4,267,269 5/1981 Grode et al. .......................... 435/2
4,360,435 11/1982 Bellamy et al. ....................... 422/1

OTHER PUBLICATIONS

Ginzburg et al., Bibl. Haemotol., 1971, No. 1, 3 pt. 2, pp. 217-220.
Wood et al., Blood, vol. 42, No. 1, 1973, pp. 17-25.
Beutler, "The Red Cell in Vitro", Grume and Stratton, N.Y., N.Y., 1974, p. 201.
Reid et al., J. Clin. Path., vol. 29, 1976, pp. 853-858.
Diepenhorst, P. et al., "Removal of Leukocytes . . . ", Vox Sang. vol. 23, pp. 308-311 (1972).
Kikugawa et al., "Filter Columns for Preparation . . . ", Vox Sang. 34; 281-290 (1978).
Lovric, V. A. et al., "Packed Red Cell Transfusions . . . ", Vox Sang. 33; 346-352 (1977).
Lovric, V. A. et al., "Improved Quality of Packed Cells", The Medical Journal of Australia, Aug. 6, 1977, pp. 183, 184 and 186.
Diepenhorst, P. et al., "Removal of Leukocytes from Whole Blood . . . ", Vox Sang. 29, pp. 15-22 (1975).

Primary Examiner—Peter Hruskoci
Assistant Examiner—W. Gary Jones
Attorney, Agent, or Firm—James A. Giblin

[57] ABSTRACT

A multiple blood bag system is disclosed having at least two blood bags and conduit means providing sealed flow communication between the bags and a filtering means integrally disposed between two of the bags for removing platelets and white cells from a red cell concentrate in the blood bag system. In the method of the invention a red cell concentrate is provided in one of the blood bags of the above system and an additive solution is mixed therewith. The mixture of the red cell concentrate and additive solution is passed through the filtering means from one of the bags to another.

5 Claims, 1 Drawing Sheet

METHOD OF REMOVING PLATELETS AND WHITE CELLS FROM A RED CELL CONCENTRATE

This application is a division of application Ser. No. 385,167 filed June 4, 1982 now U.S. Pat. No. 4,596,657.

BACKGROUND OF THE INVENTION

1. Field of the Invention

This invention relates to and has among its objects novel apparatus and methods for providing packed red blood cells (erythrocytes) which are substantially free of platelets and contain low levels of white cells and have a storage life of up to about 35 days. Further objects of the invention will be evident from the following description wherein parts and percentages are by weight unless otherwise specified.

2. Description of the Prior Art

It is desirable, for patients who require frequent blood transfusions, to remove white cells and platelets from donor blood prior to transfusion. Febrile reactions, which are usually attributable to transfused HLA antigens on white cells and platelets present in the blood may occur in 3.6% of patients infused. Such side effects are usually more frequent and severe in patients who receive multiple transfusions.

The removal of HLA antigen may be accomplished in a number of ways. Perhaps the most effective means, but unfortunately the most costly, involves the reconstitution of frozen blood.

A less expensive approach is to wash blood with saline in a number of washes. However, this saline wash approach is time consuming not only in the processing of batches but also in continuous operation. Furthermore, significant loss of red cells occurs and less predictable removal of white cells and platelets is obtained.

Kikugawa et al. in Vox Sang., Vol. 34, 281–290 (1975) describe commercial cotton wool filters for filtering blood to remove the above HLA antigen. These filters are, however, expensive and cumbersome to use.

Diepenhorst et al in Vox Sang., Vol. 23, 308–320 (1972) and Vol. 29, 15–22 (1975) disclose cotton wool filtration of blood under pressure. This method, while efficient, requires a special apparatus that is expensive.

All of the above techniques require that the treated blood be infused within 24 hours of treatment in order to avoid the potential risk of infection. Prolonged shelf life of blood so treated is not possible.

SUMMARY OF THE INVENTION

The invention described herein provides for apparatus and methods for preparing red blood cells which are substantially free of platelets and contain low levels of white cells (thus preventing formation of microaggregates) and have a storage life of at least about 21 days, preferably up to about 35 days, depending on the nature of the anticoagulant and red cell storage solution employed.

The apparatus of the invention comprises a multiple closed blood bag system having at least two blood bags and conduit means providing sealed flow communication between the bags. A filtering means is integrally disposed between two of the blood bags.

In the method of the invention a red cell concentrate is provided in a blood bag of a multiple blood bag system comprising at least two blood bags and conduit means providing sealed flow communication between said bags and a filtering means integrally disposed between two of the bags. The red cell concentrate is mixed with an additive solution and the mixture is passed through the filtering means from one of the bags to the other. The filtering means is designed to remove platelets and white cells, and thus prevent formation of microaggregates in the red cell concentrate.

The primary advantage of the present invention is its simplicity and its effectiveness. The apparatus of the invention is easy and inexpensive to use. A further advantage of the invention is that the red cells prepared as above have an extended storage life of at least about 21 days or more. Above all, the filtered red blood cells are essentially free of platelets and have very low levels of white cells and microaggregates, thus reducing the incidence of febrile reactions or HLA sensitization in the infusion of the treated red cells.

The blood bag system having an integral filter assures that sterility will not be breached during the filtering operation. Prolonged shelf life is assured, and there is no added risk of infection.

DESCRIPTION OF THE PREFERREED EMBODIMENTS

In a preferred embodiment the multiple blood bag system of the invention comprises at least three bags, a primary bag and at least two satellite bags, connected by conduit means providing sealed flow communication between the bags and a filtering means integrally disposed between two of the bags. Red blood cells in the multiple blood bag system may be passed from one of the bags to another through the filtering means comprising a housing containing a filtering medium which removes platelets and white cells and provides extended storage life of the red cells when the red cell concentrate is mixed with an additive solution, e.g., a red cell storage solution, prior to filtration by introducing the additive solution into the red cell concentrate.

In the method of the invention whole blood is introduced, e.g., by collection from a donor, into the primary bag of the above system. After centrifugation, plasma is expressed into one of the satellite bags which does not have a filtering means disposed between it and the primary bag. Next, the additive solution in the satellite bag that is separated from the primary bag by the filtering means is passed through the filtering means into the donor bag wherein it is mixed with the red cells. The mixture of red cells and solution is then passed back through the filtering means into the satellite bag in which they may be stored for extended periods. The so-treated red cells are substantially free of platelets (i.e., containing less than 10% of the original platelets) and of white cells (i.e., containing less than 10% of the original white cells); also microaggregate formation is virtually eliminated.

Figure 1:
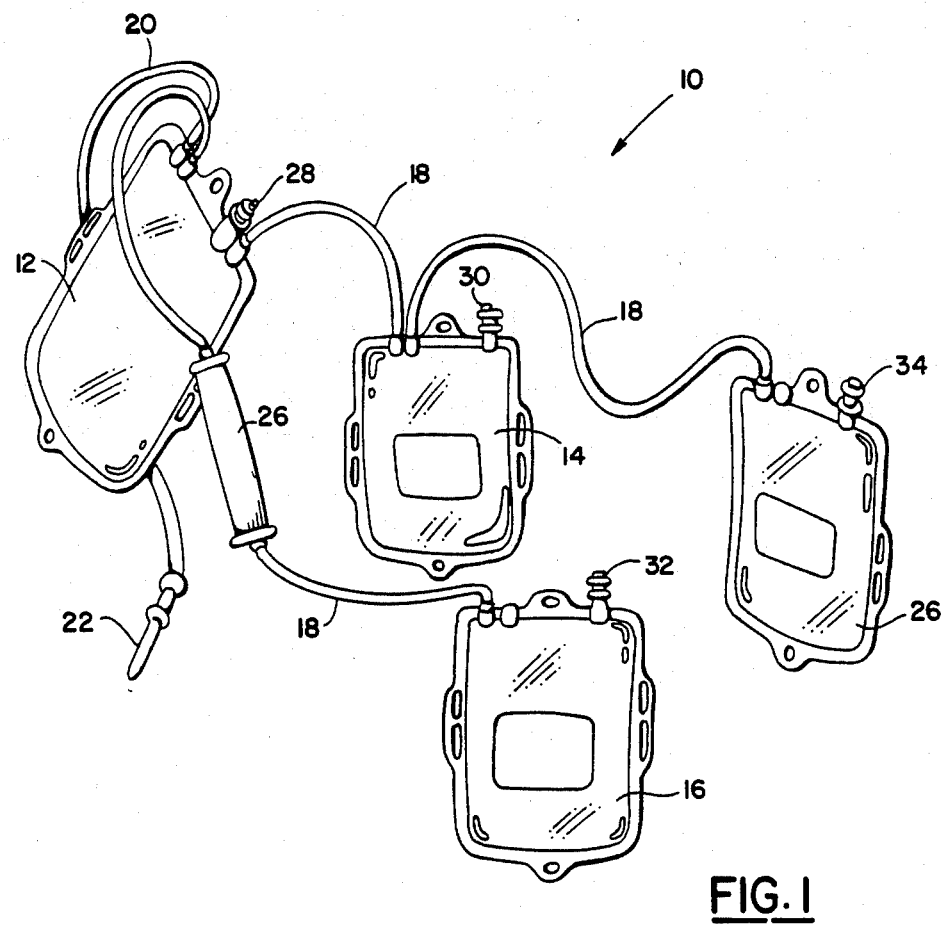
FIG. 1 is a three-dimensional depiction of an apparatus in accordance with the present invention.
Figure 2:
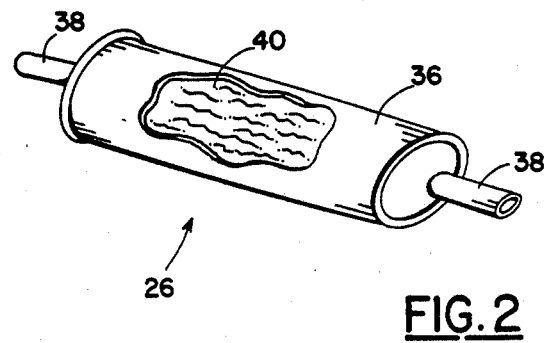
FIG. 2 is a three-dimensional depiction of a filtering means in accordance with the invention.

The apparatus and method of the invention will next be described in detail with reference to FIGS. 1 and 2.

Blood bag system 10 includes primary or donor bag 12 connected to satellite bags 14 and 16 by means of flexible tubing or conduit means 18, which provides sealed flow communication between 12 and 14 and 16. Bag 12 is adapted for receiving blood from a donor and includes blood collection tube 20 and donor needle 22. Satellite bag 24 is connected to bag 14 by means of flexible tubing 18.

Fluid flow through tubing 18 is controlled by conventional valving means such as snap-off plugs, removable plugs, or slide clamps. Conventional access ports 28, 30, 32, and 34 are found on bags 12, 14, 16, and 24, respectively, which may also contain other design features known in the art.

The blood bags of system 10 may be of conventional construction being made of a plastic material that is blood compatible, flexible, translucent, and sterilizable. The plastic may be a polyvinylchloride, polyester, polyolefin, polyurethane, and so forth and may include blends of the above materials. Flexible tubing 20 and 18 may be made of a plastic material that is the same as or different from the plastic material of the blood bags.

Filtering means 26 is integrally disposed between bags 12 and 16 and is attached at its ends to tubing 18. Filtering means 26 includes a housing 36 made of rigid polyvinylchloride or the like and tubing fitments 38. Filtering means 26 is filled with a filtration medium 40 such as cotton wool or cellulose acetate or other synthetic fibers such as polyester, polyamides, and the like. Preferred filtration medium for purposes of this invention is either cotton wool as prepared by the method of Diepenhorst et al referred to above (incorporated herein by reference) or cellulose acetate. The amount of filtration medium depends upon the amount of red cells to be filtered. Usually about 20-50 grams of filtration medium are employed per 200-250 ml of red cell concentrate.

Bag 16 contains an additive solution for mixing with the red cells to be filtered to prolong the storage life of the red cells. This additive solution may be, for example, a conventional red cell storage solution such as that described in Ginzburg et al, Bibl. Haemotol., 1971, No. 3, Pt. 2, 217-220; Wood et al, Blood, Vol. 42, No. 1, 1973, 17-25; Beutler, "The Red Cell in Vitro" Grum and Stratton, New York, N.Y., 1974, p. 201; Lovric et al, Medical Journal of Australia, Vol. 2, 183-186, 1977; U.S. Pat. No. 4,267,269; in an amount of about 50-100 ml per 200-250 ml of red cell concentrate.

In use, blood is collected into bag 12 through donor tube 20 under conventional conditions. Donor bag 12 may contain an anticoagulant such as Adenine-Citrate-Dextrose (ACD), Citrate-Phosphate-Dextrose (CPD), Citrate Phosphate-277 millimoles Dextrose (CP2D), CPD plus adenine, or other conventional anticoagulant, with which the collected blood mixes. The collected blood may then be processed directly or stored usually at about 4°-6° C. At processing, bag system 10 is centrifuged as is customary in the art causing the red cells in the blood in bag 12 to settle at the bottom of the bag. Blood plasma is expressed by conventional techniques from 12 into 14 from which fresh plasma and a platelet concentrate, for example, may be obtained in bags 14 and 24, respectively. Bag system 10 may optionally be equipped with other satellite bags into which other blood components may be expressed or processed as necessary or desired.

The additive solution from bag 16 is drained through filter 26 into donor bag 12 now containing the red blood cell concentrate. The red cells are back-filtered, preferably by gravity, through filter 26 into bag 16. This may be accomplished, conveniently in the refrigerator or coolroom, at a temperature of about 4°-6° C., e.g., overnight or for the period of time necessary to filter all of the red blood concentrate, usually about 2-4 hours or more.

A blood bag system with only two blood bags in sealed flow communication and an integral filtering means disposed between the bags is within the purview of the invention. However, in use such a system would require connection of a third receptacle to receive plasma separated from the red cell concentrate. Such connection may be made, for example, at one of the ports of the donor bag by means, for example, of a sterile connector having a third bag attached thereto for receiving plasma.

EXAMPLE

The invention is demonstrated further by the following illustrative example.

For experimental purposes 59 units of donor blood (425-450 ml) were collected into blood bags containing 63 ml of citrate phosphate and 277 mM dextrose anticoagulant, specially designed for the purpose by Tuta Laboratories, Lane Cove, Sydney, Australia. (For purposes of carrying out these experiments the donor bag was part of a blood bag system of the type exhibited in FIG. 1 but containing an additional satellite bag integrally attached by means of flexible tubing to the donor bag.) Following centrifugation at 4,000 g for 10 minutes, the plasma was removed. The residual packed red cells were split into two halves. One half was suspended in a satellite bag containing 50 ml of an aqueous additive solution of disodium hydrogen phosphate (25 mM), adenine (0.5 mM), sodium chloride (123 mM), dextrose (40 mM), trisodium citrate (15 mM), and citric acid (9.75 mM). Control data were obtained from this portion of the packed red cells.

The test data were obtained from the other half of the packed red blood cells; the same additive solution was also contained in a satellite bag separated from the donor bag by a filter integral with the tubing connecting the donor and satellite bag. This 50-ml volume additive solution was passed through the filter into the donor bag containing the remaining half of the residual packed red cells. The filter medium comprised cotton wool (20 g) prepared by the method of Diepenhorst et al mentioned above. Next, the red cell concentrate in the donor bag was filtered overnight by gravity at 4°-6° C. through the filter and into the satellite bag integrally connected therewith.

Autologous erythrocyte survival studies (Dacie et al, "Practical Haemotology", 5th ed., Churchill Levingston, Edinburgh, 1975) were assessed in 10 volunteers following informed consent, and were determined either at 28 or 35 days of storage. Oxygen dissociation curves were drawn with the Hem-0-Scan instrument (Aminco, Silver Spring, Md.). The $P_{50}$ values were determined by first removing the supernatant after centrifugation. The packed red cells were then adjusted to a hematocrit of 40% and pH 7.4 with a reagent mixture containing AB plasma and Tris-HCL buffer (pH 9.0) and then tested immediately. Adenosine triphosphate (ATP), 2,3-diphosoglycerate (2,3-DPG) supernatant hemoglobin, pH, potassium and methylene blue uptakes were tested as described in Lovric et al, Vox Sang., Vol. 33, 346-352, 1977. Erythrocyte deformability was measured with the 5- m polycarbonate filtration method (Ried et al, J. Clin. Path., Vol. 29, 853-855, 1976) using a negative pressure of 130 mm Hg.

Microaggregate counts were done on aliquots kept between 4° and 6° C. until just prior to counting using a ZF Coulter Counter with a 200-μm orifice coupled to the Coulter Channelyzer (Coulter Electronics, Hialeah, FlA.). The packed red cells were first resuspended by gentle mixing, and a 1/100 dilution made in isotonic saline (Isoton, Coulter Electronics). Bubble formation could be avoided by first aspirating the sample into the Coulter diluter, and subsequent release near the bottom of the vessel already containing the diluent. Next, erythrocytes were lysed by adding 50 μL of 10% saponin (Fisher Scientific, Fairlawn, N.Y.) and a stop watch started. It is essential that the saponin be added slowly, the container inverted slowly twice only and without shaking, lest bubble formation preclude reproducible counts. Exactly 65 sec. after the addition of saponin the count is commenced and the mean of duplicates recorded for each of the channels. The background count values were subtracted from blanks not containing blood, but handled identically. The coefficient of variation with this procedure is less than 5%.

The results of all tests are tabularized below:

TABLE 1

| Storage | $P_{50}$ (mm Hg) | |
| (weeks) | Filtered | Control |
| --- | --- | --- |
| 0 | 27 | 26 |
| 1 | 25.5 | 24 |
| 2 | 23 | 20 |
| 3 | 22 | 19 |
| 4 | 21 | 19 |
| 5 | 20 | — |

TABLE 2

| Storage | ATP (μmol/g Hb*) | |
| (weeks) | Filtered | Control |
| --- | --- | --- |
| 0 | 4.4 | 4.4 |
| 1 | 3.8 | 3.8 |
| 2 | 3.4 | 3.0 |
| 3 | 2.7 | 2.3 |
| 4 | 2.5 | 1.8 |
| 5 | 2.2 | 1.7 |

*Hemoglobin

TABLE 3

| Storage | Supernatant Potassium (mEq/l) | |
| (weeks) | Filtered | Control |
| --- | --- | --- |
| 0 | 5 | 6 |
| 1 | 10 | 11 |
| 2 | 18 | 20 |
| 3 | 20 | 28 |
| 4 | 25 | 35 |
| 5 | 30 | 45 |

TABLE 4

| Storage | Microaggregate Counts [(10–15 μm) × $10^9$/l] | |
| (weeks) | Filtered | Control |
| --- | --- | --- |
| 0 | 10 | 300 |
| 1 | 10 | 125 |
| 2 | 10 | 375 |
| 3 | 10 | 400 |
| 4 | 10 | 375 |
| 5 | 10 | — |

TABLE 5

| Storage | Microaggregates [(15–30 μm) × $10^9$/l] | |
| (weeks) | Filtered | Control |
| --- | --- | --- |
| 0 | 10 | 15 |
| 1 | 10 | 20 |
| 2 | 10 | 25 |
| 3 | 10 | 30 |
| 4 | 10 | 35 |
| 5 | 10 | — |

TABLE 6

| Storage | Erythrocyte (5 μm) filtration rate, ml/min | |
| (weeks) | Filtered | Control |
| --- | --- | --- |
| 0 | 1.50 | .10 |
| 1 | 1.20 | .15 |
| 2 | 1.10 | .20 |
| 3 | 1.00 | .10 |
| 4 | 0.90 | .05 |
| 5 | 0.95 | — |

2,3-DPG levels fell to 20% of initial values at 3-weeks storage with a further decline at 35 days to about 12%. There was no difference in the pH values when comparing filtered to unfiltered aliquots and similarly, methylene blue uptakes were 14±2% of original levels after 35 days storage. The supernatant hemoglobin did not exceed 0.5 g/l after 35 days storage. Mean $^{51}$Cr autologous erythrocyte survivals in the 10 units of filtered blood were 85% (n=2, range 83–87%) after 28 days and 79% (n=8, range 67–91%) after 35 days storage. The loss of erythrocytes on the filter averaged 10% (range 8–15%), while trapping over 90% of white cells (range 85–99%) and all platelets. The final hematocrit of the filtered blood was in the range of 53–58%.

I claim:

1. A method for removing platelets and white blood cells from a red cell concentrate which comprises red blood cells, white blood cells and platelets, the method comprising the steps of—
   (a) Collecting the red cell concentrate into the first blood bag of a multiple blood bag system comprising a first bag and a second bag, the second bag containing a red cell storage solution, the system including a filtering means integrally disposed between the two bags;
   (b) introducing the solution through the filtering means into the first bag containing the red cell concentrate; and then
   (c) passing the red cell concentrate and solution through the filtering means from the first bag to the second bag under conditions sufficient to remove white blood cells and platelets from the red cell concentrate.

2. The method of claim 1 wherein the solution contained in the second blood bag is mixed with the red cell concentrate by passing the solution through the filtering means into the first blood bag containing the red cell concentrate.

3. A method for removing platelets and white cells from a red cell concentrate, which comprises—
   (a) collecting blood from a donor into a donor bag of a multiple blood bag system comprising at least two bags having an integral filtering means disposed between the bags, one of the bags being the donor bag and the other bag being a satellite bag which includes a red cell storage solution;
   (b) treating the collected blood in the donor bag to separate a red blood cell concentrate therefrom, the concentrate including platelets and white cells;

(c) mixing the solution from the satellite bag with the red cell concentrate by passing the solution through the filtering means and into the donor bag; and (d) passing the mixture of red cell concentrate and solution through the filtering means from the donor bag to the satellite bag to remove white cells and platelets from the concentrate.

4. The method of claim 3 wherein the filtering means comprises a housing containing a filtering medium.

5. The method of claim 4 wherein the filtering medium is selected from the group consisting of cotton wool, cellulose acetate, and synthetic fibers.

* * * * *